United States Patent [19]

Pelosi, Jr.

[11] 3,997,583
[45] Dec. 14, 1976

[54] 3'-CHLORO-4'-THIOCYANATOHYDROCINNAMANILIDE

[75] Inventor: Stanford S. Pelosi, Jr., Norwich, N.Y.

[73] Assignee: Morton-Norwich Products, Inc., Norwich, N.Y.

[22] Filed: Jan. 16, 1976

[21] Appl. No.: 649,585

[52] U.S. Cl. .................. 260/454; 424/302
[51] Int. Cl.² ....................... C07C 161/02
[58] Field of Search ...................... 260/454

[56] References Cited
UNITED STATES PATENTS

| 3,305,575 | 2/1967 | Debarrg et al. | 260/454 |
| 3,455,982 | 7/1969 | Watanabe et al. | 260/454 |
| 3,455,985 | 7/1969 | Sternbach et al. | 260/454 |

OTHER PUBLICATIONS

Wager, (Synthetic Organic Chemistry), p. 566.

Primary Examiner—Lewis Gotts
Assistant Examiner—D. R. Phillips
Attorney, Agent, or Firm—Anthony J. Franze

[57] ABSTRACT

3'-Chloro-4'-thiocyanatohydrocinnamanilide is an effective antibacterial agent.

1 Claim, No Drawings

3'-CHLORO-4'-THIOCYANATOHYDROCINNAMANILIDE

This invention relates to the compound 3'-chloro-4'-thiocyanatohydrocinnamanilide and a method for its preparation.

The compound of this invention possesses antibacterial activity. It is particularly inimical to *Staphylococcus aureus*, *Escherichia coli*, and *Hemophilus vaginalis* in the commonly employed in vitro technique for determining antibacterial activity at levels of from 1.5 to 6.25 mcg of compound per milliliter of test media. This compound is thus adapted to be combined in various forms such as ointments, powders, solutions, sprays, dusts and the like in a concentration of from 0.1 – 1% by weight suitable for application to prevent bacterial contamination.

The compound of this invention is readily prepared. Currently it is preferred to react hydrocinnamoyl chloride with 3-chloro-4-thiocyanatoaniline.

In order that this invention may be fully available to and understood by those skilled in the art, the method now preferred is briefly described.

3'-Chloro-4'-thiocyanatohydrocinnamanilide

Hydrocinnamoyl chloride (40 g, 0.24 mole) was added dropwise over 15 min to a stirred, refluxing mixture of 41 g (0.22 mole) of 3-chloro-4-thiocyanatoaniline and 48 g (0.35 mole) of anhydrous $K_2CO_3$ in 250 ml of dry acetone. The mixture was heated under reflux for 5½ hr, and 200 ml of acetone was added. The mixture was filtered, and the solvent was removed on a rotary evaporator. Crystallization of the residual oil from ethyl acetate gave 7 g of unidentified solid which was set aside. The mother liquor was concentrated on a rotary evaporator to give a residual oil which solidified on standing. Recrystallization from toluene gave 28 g (49%) of product. One additional recrystallization from toluene gave an analytical sample, m.p. 96°–98°.

Anal. Calcd. for $C_{16}H_{13}ClN_2OS$: C, 60.66; H, 4.14; N, 8.84. Found: C, 61.05; H, 4.25; N, 8.91.

What is claimed is:

1. The compound 3'-chloro-4'-thiocyanatohydrocinnamanilide.

* * * * *